United States Patent [19]

Venturello et al.

[11] Patent Number: 5,575,947
[45] Date of Patent: Nov. 19, 1996

[54] IMIDE-AROMATIC PEROXYACIDS

[75] Inventors: Carlo Venturello, Novara; Claudio Cavalotti, Milan, both of Italy

[73] Assignee: Ausimont S.r.l., Italy

[21] Appl. No.: 299,017

[22] Filed: Jan. 19, 1989

[30] Foreign Application Priority Data

Jan. 20, 1988 [IT] Italy ................................ 19132/88

[51] Int. Cl.$^6$ ................ C07D 207/40; C07D 223/10
[52] U.S. Cl. ............... 252/186.26; 8/111; 252/186.42; 548/473; 548/479
[58] Field of Search ................. 548/479, 473; 8/111; 252/186.46, 93

[56] References Cited

U.S. PATENT DOCUMENTS 5,310,938  5/1994  Cavalotti et al. .................. 548/479

FOREIGN PATENT DOCUMENTS

| 349940 | 7/1989 | European Pat. Off. . |
|---|---|---|
| 0349940 | 1/1990 | European Pat. Off. . |
| 3823172 | 1/1990 | Germany . |
| 07501 | 7/1990 | WIPO . |
| 9007501 | 7/1990 | WIPO . |
| 92/11238 | 7/1992 | WIPO . |

OTHER PUBLICATIONS

Balenovic et al, (I), "Chem. Abstracts", vol. 56, (1962) #4663e.
Balenovic et al, (II), "Chem. Abstracts", vol. 57, (1962) #15224i.

Primary Examiner—Nicholas Rizzo
Attorney, Agent, or Firm—Bryan Cave LLP

[57] ABSTRACT

Imide-aromatic (poly)peroxyacids are herein disclosed, which have the formula (I):

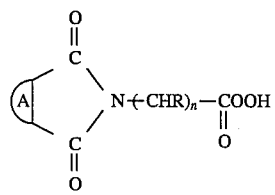

wherein A represents a residue of a substituted or unsubstituted benzene or naphthalene ring; R is a hydrogen atom, a lower alkyl group, a COOH group or a COOOH group; and n is an integer from 1 to 5.

19 Claims, No Drawings

IMIDE-AROMATIC PEROXYACIDS

DESCRIPTION OF THE INVENTION

The present invention relates to per se new organic (poly)peroxyacids, which may be referred to as imide-aromatic (poly)peroxycarboxylic acids, and to the relevant preparation process.

More particularly, the present invention relates to imide-aromatic (poly)peroxycarboxylic acids having the formula (I):

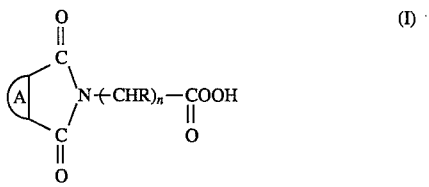

wherein A represents a residue of a substituted or unsubstituted benzene or naphthalene ring; the symbol or symbols R, which may be equal to or different from one another, represent a hydrogen atom or an optionally substituted lower alkyl group, a COOH group or a COOOH group, and n is an integer from 1 to 5.

Particularly, R represents a straight or branched $C_1$–$C_5$ alkyl group, but preferably is a hydrogen atom.

The imide-aromatic peroxycarboxylic compounds having the above-defined formula (I) are per se novel, and constitute a new class of highly interesting products from an industrial viewpoint.

They, in fact, may find a general use, similarly, to already known peroxyacids, in the field of the plastics materials as monomer polymerization initiator agents, and, in particular, as oxidizing agents for olefin epoxidation and hydroxylation, and in many other oxidative processes in the field of fine chemistry.

More specifically, for example, the imide-aromatic (poly)peroxycarboxylic acids having the above formula (I) find a particularly efficacious application in the field of bleaching, in the detergent industry.

Under this latter viewpoint, generally speaking, in the past years organic peroxyacids have aroused an increasing interest in the industrial field, due, among others, to their excellent possibilities for use as bleaching agents in compositions for medium-low temperature washing, and an even more widespread interest due to energy-saving considerations.

Therefore, a large number of literature references exist concerning the very considerable research activity aiming to find organic peroxyacid compounds endowed with the necessary requisites of bleaching activity, and, in particular, of thermal stability, these latter requisites being essential for the purposes of an industrial and widespread application of such compounds.

Therefore many either mono- or di-peroxycarboxylic, straight or cyclic, organic peroxyacids are known and used, among others, in the detergent field.

Already described peroxycarboxylic acids are, e.g., diperoxydodecanedioic acid, monoperoxyphthalic acid, diperazelaic acid, substituted diperoxyglutaric and adipic acids, etc.

One object of the present invention is therefore to provide, as per se novel compounds, imide-aromatic (poly)peroxycarboxylic acids having the above formula (I).

Another objects is to provide a simple and cheap process for the preparation of the above peroxycarboxylic acids having the formula (I).

A further object is the use of imide-aromatic peroxycarboxylic acids having the above formula (I) as bleaching agents in detergent formulations; and especially those destined for low-medium temperature use.

These, and still other objects which will become even clearer to those skilled in the art from the following detailed disclosure, are achieved, according to the present invention, by the imide-aromatic (poly)peroxycarboxylic acids having the above formula (I), and by the relevant preparation process, characterized in that a substrate selected from an imide-aromatic polycarboxylic acid and its anhydride having the structure corresponding to the desired peroxycarboxylic acid having formula (I), is reacted with concentrated $H_2O_2$, by operating in a reaction medium selected from concentrated $H_2SO_4$ add $CH_3SO_3H$ or in an alkaline medium, and in that the peroxycarboxylic acid (I) is then separated from the reaction mixture by conventional and known techniques.

In this way the peroxycarboxylic acids having the formula (I) are obtained, generally as stable solids.

The R $C_1$–$C_5$ alkyl group, may in turn be substituted with $C_1$–$C_5$ alkoxy groups, hydroxylic groups, nitro-groups and so forth, and the residue A with COOH groups, etc.

More particularly, the present invention relates to the following imide-aromatic (poly)peroxyacids having the formula (I): phthalimide-peracetic acid, 3-phthalimide-perpropionic acid, 4-phthalimide-perbutyric acid, 2-phthalimide-di-perglutaric acid, 2-phthalimide-di-persuccinic acid, 3-phthalimide-perbutyric acid, 2-phthalimide-perpropionic acid, 3-phthalimide-di-peradipic acid, naphthalimide-peracetic acid, 2-phthalimide-mono-persuccinic acid and 4-(4-percarboxy)-phthalimide-peroxybutyric acid.

As stated above, these compounds are obtained according to substantially conventional methods, by reaction of a substrate consisting of the imide-aromatic (poly)carboxylic acid (having the structure corresponding to the desired peracid having formula (I) with $H_2O_2$ in sulphuric or methanesulphonic acid and by subsequent separation and so forth, according to known techniques, or by operating in an alkaline medium, according to known methods, starting from the corresponding anhydrides.

In fact, when at least one —(CHR)— residue present in the formula of the starting substrate contains a carboxylic group, it is possible to prepare the corresponding peracids having the above formula (I), by using the relevant anhydrides.

In this case, depending on the operating conditions (acid or alkaline medium and so forth), di- or mono-peroxyacids may be selectively obtained; namely peroxyacids containing two peroxycarboxylic groups or a peroxycarboxylic group and a carboxylic group.

According to a preferred operating mode, the peroxycarboxylation reaction of the acid or poly-acid, used as the starting substrate, is carried out by gradually adding $H_2O_2$ having a concentration within the range of from approximately 70% to approximately 90% by weight, to a solution of the substrate in concentrated $H_2SO_4$, or in $CH_3SO_3H$, by maintaining the reaction temperature throughout the course of the reaction within the range of from approximately 15° to approximately 50° C., depending on the reactivity of the substrate.

The amount of $H_2SO_4$ or of $CH_3SO_3H$, determined at a concentration of 100%, is from 3 to 20 moles per mole of substrate, and is preferably from approximately 4 to 14 moles per mole of substrate.

The hydrogen peroxide is used in an amount which is in excess with respect to the substrate, and is from approximately 2 to 6 moles per mole of substrate, and preferably from approximately 2.2 and 5 moles per mole of substrate, depending on the COOH groups to be percarboxylated.

The reaction time depends on the nature of the substrate, on the operating temperature, and on the end total $H_2SO_4/H_2O$ or $CH_3SO_3H/H_2O$ molar ratio present at the end of the reaction. Said ratio is from approximately 1 to 6; and preferably between approximately 1.6 to 4, by changing the various concerned parameters.

Reaction times from approximately 30 minutes to 2 hours have been shown to be operative.

The separation of the imide-aromatic (poly)peroxyacid having formula (I) is carried out according to conventional techniques such as by the filtration of the solid precipitate obtained after treatment of the reaction mixture with an ammonium sulfate solution, or by extraction with solvents and so forth.

The imide-aromatic (poly)peroxyacids having the above formula I are thus obtained in the form of crystalline solids.

The substrates, used as the starting materials are per se known compounds, or can be prepared according to conventional techniques. Suitable substrates are shown to be, for exemplary purposes: phthalimide-acetic acid, 3-phthalimide-propionic acid, 4-phthalimide-butyric acid, 2-phthalimide-glutaric acid and the corresponding anhydride, 2-phthalimide-succinic acid and the corresponding anhydride, 3-phthalimide-butyric acid, 2-phthalimide-propionic acid, 3-phthalimide-adipic acid, naphthalimide-acetic acid, 4-(4-carboxy)-phthalimide-butyric acid, and so forth, from which the above preferred peracids of formula (I) are obtained.

The peroxycarboxylic acid products having formula (I) are usually solid at room temperature.

According to the present invention, they may be especially useful in formulations of detergent compositions, e.g., granular formulations, as bleaching agents in solution over a wide temperature range, e.g., from approximately 20° to 90° C.

Therefore, the imide-aromatic peroxyacids of the present invention may be used as bleaching agents directly alone, e.g., separately from the detergent composition, or, preferably, associated with and incorporated into conventional detergent compositions, which operate within the above temperature range, and containing other components and/or additives such as e.g. builders, surfactants, soaps, zeolites, hydrotropic agents, corrosion inhibitors, enzymes, optical brighteners, stabilizers, other brightener compounds, and so forth.

Preferably, the operating temperature is from room temperature to approximately 65° C.

The preparation and use processes of the compositions as well as their formulations are in the described and/or conventional fields.

The imide-aromatic peroxyacids of the present invention may be used in combination with solid or liquid detergent compositions, and/or in the presence of other bleaching compounds. Further, the imide-aromatic peroxyacids may be subjected to a phlegmatization process, according to known art.

The present invention is now disclosed in still further detail in the following examples, which are supplied for merely illustrative and not limiting purposes.

The products prepared in the examples were characterized by elemental analysis, by determining their content of active oxygen (by iodometric titration), and by using Fourier Transform Infrared Spectroscopy (FT-IR).

EXAMPLE 1

330/g (3.434 mole) of methanesulphonic acid were charged into a beaker, equipped with stirrer, thermometer, and outer bath.

The internal temperature was increased to 25° C. and 55 g (0.268 mole) of phthalimide-acetic acid were added under stirring for 15 minutes.

The temperature was then lowered to 10° C. and 44 g of $H_2O_2$ at 70% (0.906 mole) were gradually added under stirring so that the temperature was maintained lower than 15° C.

The stirring was continued at 15° C. for 1.5 hours. At the end, the reaction mixture was poured into 600 ml of $(NH_4)_2SO_4$ at 20% maintained under stirring at 5° C.

The stirring was continued for 15 minutes at a temperature between 5° and 10° C.

The solid product was filtered under vacuum over a porous septum. The thus obtained product was suspended in 400 ml of $Na_2SO_4$ at 8% and neutralized at pH 6 by $Na_2CO_3$ at 15%.

The resulting solid was then again filtered, washed with (100 ml) ice water, wiped and dried on a porous plate inside a $CaCl_2$-drier under vacuum (2 mm Hg) at room temperature.

58 g of substantially pure phthalimide-peracetic acid were obtained. Yield: 97%.

The product may be recrystallized by dissolving it in ethyl acetate and by adding petroleum ether up to solution turbidity.

Elemental Analysis

Computed for $C_{10}H_7O_5N$: C: 54.30%; H: 3.19%; N: 6.33%; O (active): 7.23%.

Found: C: 54.32%; H: 3.33%; N: 6.57%; O (active): 7.2%.

Melting Point: 118° C. (with decomposition).

EXAMPLE 2

28 g (0.274 mole) of $H_2SO_4$ at 96% were charged into a beaker equipped with stirrer, thermometer and outer bath.

The inner temperature was brought to 25° C. and 11.7 g (0.0534 mole) of 3-phthalimide-propionic acid were added under stirring for 15 minutes.

The temperature was lowered to 10° C. and 5.2 g of $H_2O_2$ at 70% (0.107 mole) were gradually added under stirring so that the temperature was maintained lower than 15° C.

The stirring was continued at 15°0 for 1.5 hours. At the end, the reaction mixture was then poured into 80 ml of $(NH_4)_2SO_4$ at 20% maintained under stirring at 5° C.

The stirring was continued for 15 minutes at a temperature from 5° to 10° C. The solid product was filtered under vacuum over a porous septum.

The obtained product was suspended into 50 ml of $Na_2SO_4$ at 8% and neutralized at pH 6 with $Na_2CO_3$ at 15%. The resulting solid was again filtered, washed with 20 ml of ice water, wiped and dried on a porous plate into a $CaCl_2$-drier under vacuum (2 Hg mm) at room temperature.

11.3 g of substantially pure 3-phthalimide-perpropionic acid were obtained. Yield: 90%.

The product may be recrystallized as described in Example 1.

Elemental Analysis

Computed for $C_{11}H_9O_5N$: C: 56.17%; H: 3.85%; N: 5.95%; O (active): 6.80%.

Found: C: 56.83%; H: 4.01%; N: 6.10%; O (active): 6.79%.

Melting point: 91° C. (with decomposition).

EXAMPLE 3

The procedures of Example 2 were repeated by replacing 3-phthalimide-propionic acid with 4-phthalimide-butyric acid (15 g; 0.0643 mole), and by using 30 g of $H_2SO_4$ at 96% (0.294 mole), 7 g of $H_2O_2$ at 70% (0.144 mole), and by prolonging the reaction time to 2 hours.

14.5 g of substantially pure 4-phthalimide-perbutyric acid were obtained. Yield: 90%.

The product may be recrystallized as described in Example 1.
Elemental Analysis:
Computed for $C_{12}H_{11}O_5N$: C: 57.83%; H: 4.45%;N: 5.62%; O (active): 6.42%.
Found: C: 57.98%; H: 4.52%; N: 5.69%; O (active): 6.41%.
Melting Point: 103° C. (with decomposition).

EXAMPLE 4

The procedures of Example 1 were repeated by replacing phthalimide-acetic acid with 2-phthalimide-glutaric acid (6 g; 0.0216 mole), and by using 28 g (0.291 mole) of methanesulphonic acid and 3.5 g of $H_2O_2$ at 85% (0.0875 mole).

At the end, 15 ml of $(NH_4)_2SO_4$ at 40% were gradually added, so that the temperature was maintained at between 0° and 5° C., to the reaction mixture cooled at 0° C.

The resulting mixture was extracted with $Et_2O$ (6×30 ml).

The ether extract was washed with 30 ml of $(NH_4)_2SO_4$ at 40%, dried on anhydrous $Na_2SO_4$, filtered and evaporated.

An oil was obtained which was dissolved into $Et_2O$ (20 ml) and precipitated, in the solid state, by petroleum ether (40 ml), by maintaining the mixture under agitation up to complete solidification.

After filtration, 5.8 g of 2-phthalimide-diperglutaric acid at 95% were obtained. Yield: 82%.

The product was recrystallized as described in Example 1.
Elemental Analysis:
Computed for $C_{13}H_{11}O_8N$; C: 50.49%; H: 3.58%; N: 4.53%; O (active): 10.34%.
Found: C: 49.96%; H: 3.75%; N: 4.70%; O (active): 10.33%.
Melting Point: 112° C. (with decompression).

EXAMPLE 5

The procedures of Example 4 were repeated by replacing the 2-phthalimide-glutaric acid with 2-phthalimide-succinic acid (5 g; 0.019 mole) and by using 20 g (0.208 mole) of methanesulphonic acid, 3,8 g (0.095 mole) of $H_2O_2$ at 85%, and by extending the reaction time to 2 hours.

At the end, 80 ml of $(NH_4)_2SO_4$ at 40% were gradually added, so that the temperature was maintained at between 0° and 5°0, to the reaction mixture cooled at 0° C.

The stirring was continued for 15 minutes always at 0° to 5° C.

The operating procedures of Example 2 were then followed.

4 g of substantially pure 2-phthalimide-dipersuccinic acid were obtained. Yield 71%.

The product may be recrystallized as described in Example 1.
Elemental Analysis:
Computed for $C_{12}H_9O_8N$: C: 48.82%; H: 3.07%; N: 4.74%; O (active): 10.84%.
Found: C: 48.44%; H: 3.22%; N: 4.88%; O (active) 10.82%.
Melting Point: 131° C. (with decomposition).

EXAMPLE 6

The procedures of Example 5 were repeated, by replacing 2-phthalimide-succinic acid with 2-phthalimide-succinic anhydride (2 g; 0.0082 mole), and by using 10 g (0.104 mole) of methanesulphonic acid and 1.3 g (0.0325 mole) of $H_2O_2$ at 85%, and by reducing the reaction time to 1.5 hours.

At the end, 60 ml of $(NH_4)_2SO_4$ at 20% were gradually added, so that the temperature was maintained at between 0° and 5° C., to the reaction mixture cooled at 0° C.

The resulting mixture was extracted with $EtOAc/Et_2O$ 1:2 (2×30 ml). The organic extract was washed with 20 ml of $(NH_4)_2SO_4$ at 20%, dried on anhydrous $Na_2SO_4$, filtered and evaporated under vacuum.

1.8 g of 2-phthalimide-dipersuccinic acid were obtained at 95%.

Found: O (active): 10.3%; O (active) computed for $C_{12}H_9O_8N$: 10.84%.

EXAMPLE 7

5 g of a $Na_2CO_3$ solution at 17.4% were charged into a 50 ml beaker. The inner temperature was brought to 5° C. and 0.8 g of $H_2O_2$ at 85% and 0.04 g of $MgSO_4.7 H_2O$ were charged.

By maintaining the temperature at 5° C., 2 g of 2-phthalimide-succinic anhydride (0.0082 mole) were successively and rapidly charged.

The inner temperature was left to gradually increase to 20° C. by continuing the stirring for 30 minutes.

30 ml of ethyl ether and 4.2 g of $H_2SO_4$ at 20% were then added. The ether layer was successively separated and washed with $(NH_4)_2SO_4$ at 40% (2×20 ml); it was dried on anhydrous $Na_2SO_4$ and then, after the filtration of the sulphate, the peracid was precipitated with 30 ml of petroleum ether, by stirring the mixture at room temperature for 30 minutes. The peracid was filtered and again dried under vacuum at room temperature.

1.5 g of product at 63% as 2-phthalimide-monopersuccinic acid were obtained;
Found: O (active): 3.6%; O (active) computed for $C_{12}H_9NO_7$: 5.73%.

EXAMPLE 8

1.5 g of $H_2O_2$ at 85% (0.0375 mole) was added to 2 g of 4-(4-carboxy)-phthalimide butyric acid (0.0072 mole) in 12 g of methanesulphonic acid (0.125 mole) suspension, under stirring at 15° to 20° C.

Stirring was continued for 2 hours at 15° C.

The reaction product was then poured into 40 ml of $(NH_4)_2SO_4$ at 40%, maintained at 5° C. and, after 15 minutes stirring, the separated solid product was filtered. This latter was then neutralized at pH 6, by suspending it in an 8% $Na_2SO_4$ solution and by adding $Na_2CO_3$ at 15%.

The resulting solid was again filtered, washed with ice water (30 ml), and dried over a porous plate in a $CaCl_2$-drier.

The product may be recrystallized by dissolving it in ethyl acetate at room temperature and again precipitating by adding petroleum ether.

There were thus obtained 2 g of substantially pure 4-(4-percarboxy)-phthalimide peroxybutyric acid. Yield: 90%.
Elemental Analysis
Computed for $C_{13}H_{11}O_8N$; C: 50.49%; H: 3.58%; N: 4.53%; O (active): 10.35%.

Found: C: 50.04%; H: 3.75%; N: 4.48%; O (active): 10.34%.

Melting point: 109° C. (with decomposition).

EXAMPLES 9–12 (Application Examples)

Bleaching tests were carried out in the same concentration of active oxygen in the bleaching solution, and by using the imide-aromatic peroxyacid, as in the present invention, shown in the following Table I, as compared to H.48 peracid product (Mg salt of monoperphthalic acid), manufactured by INTEROX Chemical Ltd., London, United Kingdom for the detergency field.

The procedure was as follows: All tests were carried out at the constant temperature of 60° C., with an initial concentration of total active oxygen in the bleaching equal for all products, and equal to 200 mg/l.

Process

For each test, 500 ml of deionized water, contained in a 1,000 ml flask equipped with a condenser, was heated to a temperature of 60° C. and adjusted to a pH value of 9.5 (with a few drops of an NaOH solution); then the bleaching product was added with stirring with such amounts thereof being added as shown in the following Table I, and immediately thereafter, two cotton specimens of 10 cm×10 cm stained with standard stains of red wine at EMPA INSTITUTE of St. Gallen (Switzerland), and marked with the "EMPA 114" mark ##were added.

The system was subsequently kept under stirring for 60 minutes and, at the end of this time, the specimens, rinsed under running water, were dried and ironed, and were then submitted to the evaluation of the bleaching effect by means of measurements of degree of whiteness degree by reflectometry. The results are reported in the following Table I, wherein the data are expressed as Bleaching %, defined as:

$$\text{Bleaching \%} = \frac{A - B}{C - B} \times 100$$

wherein:

A=degree of whiteness (%) of the specimen bleached during the test;

B=degree of whiteness (%) of the specimen before the test;

C=degree of whiteness (%) of the completely bleached specimen, and wherein the degrees of whiteness were measured by means of an Elrepho Zeiss reflectometer, assuming MgO=100% of whiteness, and using a filter N. 6 (λ=464 mm).

The data obtained show that the peracids of the present invention have a bleaching power in an amount which may be compared with that of H.48 and in some cases even higher than that of H.48.

TABLE 1

| Compound | Amounts used in the test (grams) | Initial concentration of total active oxygen (mg/l) | Bleaching % |
| --- | --- | --- | --- |
| Example 1 (titer: 7.2% active oxygen) | 1.46 | 200 | 83.6 |
| Example 2 (titer: 6.79% of active oxygen) | 1.47 | 200 | 83.0 |
| Example 3 (titer: 6.41% of active oxygen) | 1.56 | 200 | 79.4 |

TABLE 1-continued

| Compound | Amounts used in the test (grams) | Initial concentration of total active oxygen (mg/l) | Bleaching % |
| --- | --- | --- | --- |
| Example 4 (titer: 9.81% of active oxygen) | 1.02 | 200 | 74.0 |
| Example 5 (titer: 10.82% of active oxygen) | 0.924 | 200 | 75.0 |
| H.48 (titer: 5.5% of active oxygen) | 1.86 | 200 | 75.1 |

What is claimed is:

1. Aryl-imido (poly)-peralkanoic acids of formula:

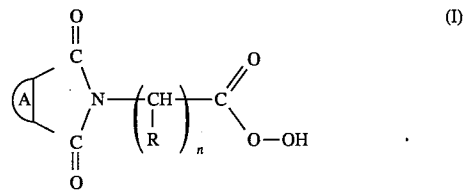

wherein n is an integer from 1 to 5, where

A represents a residue of a benzenic or naphthalenic ring, optionally substituted by a carboxylic group or a COOOH group;

the symbol or symbols R, when n is greater than 1, said symbols R may be equal or different from each other, is (are) selected from a) hydrogen;

b) carboxylic group (—COOH);

c) per-carboxylic group

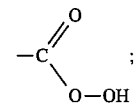

d) lower alkyl groups, substituted by a substituent selected from i) OH, NO₂ and —COOH (carboxylic group);

ii)

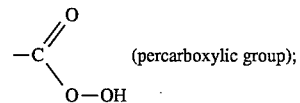

iii) lower alkoxy group.

2. Aryl-imido (poly)-peralkanoic acid according to claim 1, having formula (I) wherein the residue R, which may be equal or different from each other, are straight or branched alkyl groups containing from 1 to 5 carbon atoms.

3. A compound: phthalimide-peracetic acid.

4. A compound: 3-phthalimide-perpropionic acid.

5. A compound: 4-phthalimide-perbutyric acid.

6. A compound: 2-phthalimide-diperglutaric acid.

7. A compound: 2-phthalimide-dipersuccinic acid.

8. A compound: 2-phthalimide-mono-persuccinic acid.

9. A compound: 3-phthalimide-perbutyric acid.

10. A compound: 2-phthalimide-perpropionic acid.

11. A compound: 3-phthalimide-diperadipic acid.

12. A compound: naphthalimide-peracetic acid.

13. A compound: 4-(4-percarboxy)-phthalimide-peroxybutyric acid.

14. Aryl-imido (poly)-peralkanoic acid according to claim 1, wherein the residue R is hydrogen.

15. Aryl-amido (poly)-peralkanoic acid according to claim 1, having formula (I) wherein A represents a residue of a benzene or naphthalene ring substituted by a COOH group, the symbol or symbols R, which may be equal or different from each other, represent a hydrogen atom, a lower alkyl group substituted by at least one substituent selected from the class consisting of OH, NO$_2$, lower alkoxy group containing from 1–5 carbon atoms, a COOH group, or a COOOH group.

16. A bleaching, oxidizing or cleaning composition which contains an imidopercarboxylic acid of the formula

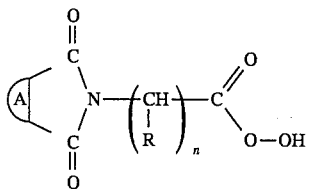
(I)

wherein:

n is an integer from 1 to 5;

A represents a residue of a benzenic or naphthalenic ring, optionally substituted by a carboxylic group or a COOOH group;

the symbol or symbols R, when n is greater than 1, said symbols R may be equal or different from each other, and may be a) hydrogen;

b) carboxylic group (—COOH);

c) percarboxylic group

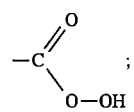

d) lower alkyl groups, substituted by a substituent selected from i) OH, NO$_2$ and —COOH;

ii)

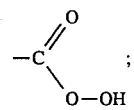

iii) lower alkoxy group.

17. Aryl-amido (poly)-peralkanoic acid according to claim 14, wherein A is a benzene ring.

18. Aryl-amido (poly)-peralkanoic acid according to claim 17, wherein n is 5.

19. Method of bleaching comprising treating an object to be bleached with an imide-aromatic (poly)percarboxylic acid having the formula (I) as bleaching agent alone or in liquid or solid detergent formulations, containing other components and/or additives, builder, surfactants, soaps, zeolites, hydrotropic agents, corrosion inhibitors, enzymes, optical bleaching agents, stabilizers and other peroxidic compounds.

* * * * *